US00PP22951P2

(12) United States Plant Patent
Wilcher et al.

(10) Patent No.: US PP22,951 P2
(45) Date of Patent: Aug. 14, 2012

(54) ***NYSSA* PLANT NAMED 'NSUHH'**

(50) Latin Name: *Nyssa sylvatica*
Varietal Denomination: Nsuhh

(75) Inventors: Clayton Wilcher, Rock Island, TN (US); Alex Neubauer, Belvidere, TN (US)

(73) Assignee: Athena Trees, Inc., Hawkinville, GA (US)

( * ) Notice: Subject to any disclaimer, the term of this patent is extended or adjusted under 35 U.S.C. 154(b) by 0 days.

(21) Appl. No.: 12/931,630

(22) Filed: Feb. 3, 2011

(51) Int. Cl.
*A01H 5/00* (2006.01)

(52) U.S. Cl. ..... Plt./216

(58) Field of Classification Search ..... Plt./216
See application file for complete search history.

*Primary Examiner* — Susan McCormick Ewoldt
(74) *Attorney, Agent, or Firm* — C. A. Whealy

(57) ABSTRACT

A new and distinct cultivar of *Nyssa* plant named 'Nsuhh', characterized by its upwardly sweeping lateral branches forming a tight pyramidal plant form; rapid growth rate; glossy dark green-colored leaves that maintain glossy dark green coloration throughout the summer; and resistance to leaf spot.

3 Drawing Sheets

Botanical designation: *Nyssa sylvatica.*
Cultivar denomination: 'NSUHH'.

BACKGROUND OF THE INVENTION

The present invention relates to a new and distinct cultivar of *Nyssa* plant, botanically known as *Nyssa sylvatica*, commercially referred to as Black Gum and hereinafter referred to by the name 'Nsuhh'.

The new *Nyssa* plant originated from an open-pollination in Rock Island, Tenn. of an unnamed selection of *Nyssa sylvatica*, not patented, as the female, or seed, parent with an unknown selection of *Nyssa sylvatica* as the male, or pollen, parent. The new *Nyssa* plant was discovered and selected by the Inventors as a single plant from within the progeny of the stated open-pollination in a controlled environment in Rock Island, Tenn. in 2002.

Asexual reproduction of the new *Nyssa* plant by chip budding in a controlled environment in Belvidere, Tenn. since August, 2003, has shown that the unique features of this new *Nyssa* plant are stable and reproduced true to type in successive generations.

SUMMARY OF THE INVENTION

Plants of the new *Nyssa* have not been observed under all possible environmental and cultural conditions. The phenotype may vary somewhat with variations in environmental conditions such as temperature and light intensity without, however, any variance in genotype.

The following traits have been repeatedly observed and are determined to be the unique characteristics of 'Nsuhh'. These characteristics in combination distinguish 'Nsuhh' as a new and distinct *Nyssa* plant:

1. Upwardly sweeping lateral branches forming a tight pyramidal plant form.
2. Rapid growth rate.
3. Glossy dark green-colored leaves that maintain glossy dark green coloration throughout the summer.
4. Resistant to leaf spot.

Plants of the new *Nyssa* can be compared to plants of the female parent selection. Plants of the new *Nyssa* differ primarily from plants of the female parent selection in branch angle as plants of the new *Nyssa* have more upwardly sweeping lateral branches than plants of the female parent selection.

Plants of the new *Nyssa* can also be compared to plants of *Nyssa sylvatica* 'Wildfire', not patented. Plants of the new *Nyssa* and 'Wildfire' differ in the following characteristics:

1. Plants of the new *Nyssa* have more upwardly sweeping lateral branches as plants of 'Wildfire' have laterally-orientated lateral branches.
2. Plants of the new *Nyssa* have glossier and more durable leaves than plants of 'Wildfire'.

BRIEF DESCRIPTION OF THE PHOTOGRAPHS

The accompanying colored photographs illustrate the overall appearance of the new *Nyssa* plant showing the colors as true as it is reasonably possible to obtain in colored reproductions of this type. Colors in the photographs may differ slightly from the color values cited in the detailed botanical description which accurately describe the colors of the new *Nyssa* plant.

The photograph on the first sheet comprises a side perspective view of typical trees of 'Nsuhh' grown in an outdoor nursery.

The photograph on the second sheet is a close-up view of the upper (left) and lower (right) surfaces of typical leaves of 'Nsuhh'.

The photograph on the third sheet comprises a close-up view of a typical tree of 'Nsuhh' grown in an outdoor nursery during the autumn showing the fall leaf coloration.

DETAILED BOTANICAL DESCRIPTION

The aforementioned photographs and following observations, measurements and values describe plants grown during the summer and autumn in an outdoor nursery in Hawkinsville, Ga. and under commercial practices. Trees were five years old when the photographs and description were taken. In the following description, color references are made to The Royal Horticultural Society Colour Chart, 2001 Edition, except where general terms of ordinary dictionary significance are used.

Botanical classification: *Nyssa sylvatica* 'Nsuhh'.

Parentage:

*Female, or seed, parent*.—Unnamed selection of *Nyssa sylvatica*, not patented.

*Male, or pollen, parent*.—Unknown selection of *Nyssa sylvatica*, not patented.

Propagation:

*Type*.—By chip budding.

Plant description:

*Plant and growth habit*.—Upright tree with upwardly sweeping lateral branches forming a tight pyramidal plant form; freely branching habit with numerous lateral branches developing per plant; vigorous growth habit and rapid growth rate with trees growing 106.7 cm per year.

*Plant height*.—About 4.88 meters.

*Plant diameter*.—About 2.13 meters.

*Trunk diameter, about* 30 *cm above ground level*.—About 9.1 cm.

*Texture, bark*.—Woody, fissured.

*Color, bark*.—Close to 197A.

*Lenticels*.—Length: About 1 mm. Width: About 1.5 mm to 3 mm. Color: Close to 156A.

Lateral branch description:

*Diameter, about* 2.5 *cm below terminal bud*.—About 2.5 mm.

*Internode length*.—About 3.8 cm to 5.1 cm.

*Strength*.—Strong.

*Aspect*.—Upwardly sweeping, about 30° to 70° from vertical.

*Texture*.—Smooth, glabrous.

*Color, new growth*.—Close to 144B.

*Color, first year wood*.—Close to 165A.

*Lenticels, new growth*.—Length: About 0.5 mm. Width: About 0.5 mm. Color: Close to 159D.

*Lenticels, first year wood*.—Length: About 1 mm. Width: About 1 mm. Color: Close to 159A.

Foliage description:

*Arrangement*.—Alternate, simple.

*Developing leaves*.—Length: About 6 cm. Width: About 3 cm. Shape: Obovate. Apex: Acute to acuminate. Base: Acute. Margin: Entire. Texture, upper surface: Smooth, glabrous. Texture, lower surface: Pubescence along the veins and margins. Venation pattern: Pinnate. Color: Upper surface: Close to 144A; venation, close to 138C. Lower surface: Close to 138B; venation, close to 144B. Petioles: Length: About 6 mm. Diameter: About 1.25 mm. Texture, upper surface: Smooth, glabrous. Texture, lower surface: Pubescent.

*Fully expanded leaves*.—Length: About 8.4 cm. Width: About 4.1 cm. Shape: Obovate. Apex: Acute to acuminate. Base: Acute. Margin: Entire. Texture, upper surface: Smooth, glabrous; glossy. Texture, lower surface: Sparse pubescence along the veins and margins. Venation pattern: Pinnate. Color: Upper surface: Close to 147A; venation, close to 145A; during the autumn, color becoming closer to 45A and 34A. Lower surface: Close to 191A; venation, close to 196A; during the autumn, color becoming closer to 182B and 181D. Petioles: Length: About 1 cm. Diameter: About 1.5 mm. Texture, upper surface: Pubescent. Texture, lower surface: Smooth, glabrous. Color, upper surface: Close to 145A occasionally blushed with close to 182A. Color, lower surface: Close to 145A.

Bud description:

*Terminal buds*.—Length: About 5.9 mm. Diameter: About 4.1 mm. Color: Close to 200A.

*Lateral buds*.—Length: About 4.4 mm. Diameter: About 2.9 mm. Color: Close to 200A.

Flower description:

*Flower arrangement and habit*.—Dioecious; male flowers only; flowers simple and inconspicuous; flowers arranged in oval to rounded racemes with usually about ten to twelve flowers per raceme.

*Fragrance*.—None detected.

*Natural flowering season*.—Plants of the new *Nyssa* begin flowering in late April in Hawkinsville, Ga.

*Flower longevity*.—Individual flowers last about ten days to two weeks on the plant; flowers not persistent.

*Inflorescence height*.—About 3.2 cm.

*Inflorescence diameter*.—About 1.7 cm.

*Flower diameter*.—About 6 mm.

*Flower length* (*depth*).—About 3.5 mm.

*Petals*.—None observed.

*Sepals*.—Quantity and arrangement: About eight sepals arranged in a single whorl. Length: About 1 mm. Width: About 0.5 mm. Shape: Ovate. Apex: Acute; reflexing. Margin: Entire. Texture, upper and lower surfaces: Smooth, glabrous. Color: When opening, upper and lower surfaces: Close to 145A. Fully opened, upper and lower surfaces: Close to 145A.

*Peduncles*.—Length: About 2.6 cm. Diameter: About 1 mm. Strength: Strong. Texture: Smooth, glabrous. Color: Close to 144B.

*Pedicels*.—Length: About 5.5 mm. Diameter: About 0.5 mm. Strength: Strong. Texture: Smooth, glabrous. Color: Close to 144B.

*Reproductive organs*.—Stamens: Quantity: About ten to twelve per flower. Before anthesis: Filament length: About 1.5 mm. Filament color: Close to 145A. Anther length: About 1.25 mm. Anther diameter: About 1 mm. Anther color: Close to 145A. During anthesis: Filament length: About 3 mm. Filament color: Close to 145A. Anther length: About 1 mm. Anther diameter: About 0.75 mm. Anther color: Close to 158D. Pollen amount: About 32 grains per 1 $mm^2$. Pollen color: Close to 2C. After anthesis: Filament length: About 3 mm. Filament color: Close to 145A. Anther length: About 0.75 mm. Anther diameter: About 0.75 mm. Anther color: Close to 146A. Pistils: None observed, male flowers only. Seeds and fruits: None observed.

Temperature tolerance: Plants of the new *Nyssa* have been observed to be hardy to USDA Hardiness Zone 4 and to USDA Heat Zone 9.

Pathogen/pest resistance: With development, plants of the new *Nyssa* have been observed to be resistant to leaf spot. Plants of the new *Nyssa* have not been observed to be resistant to pests and other pathogens common to *Nyssa* plants.

It is claimed:

1. A new and distinct *Nyssa* plant named 'Nsuhh' as illustrated and described.

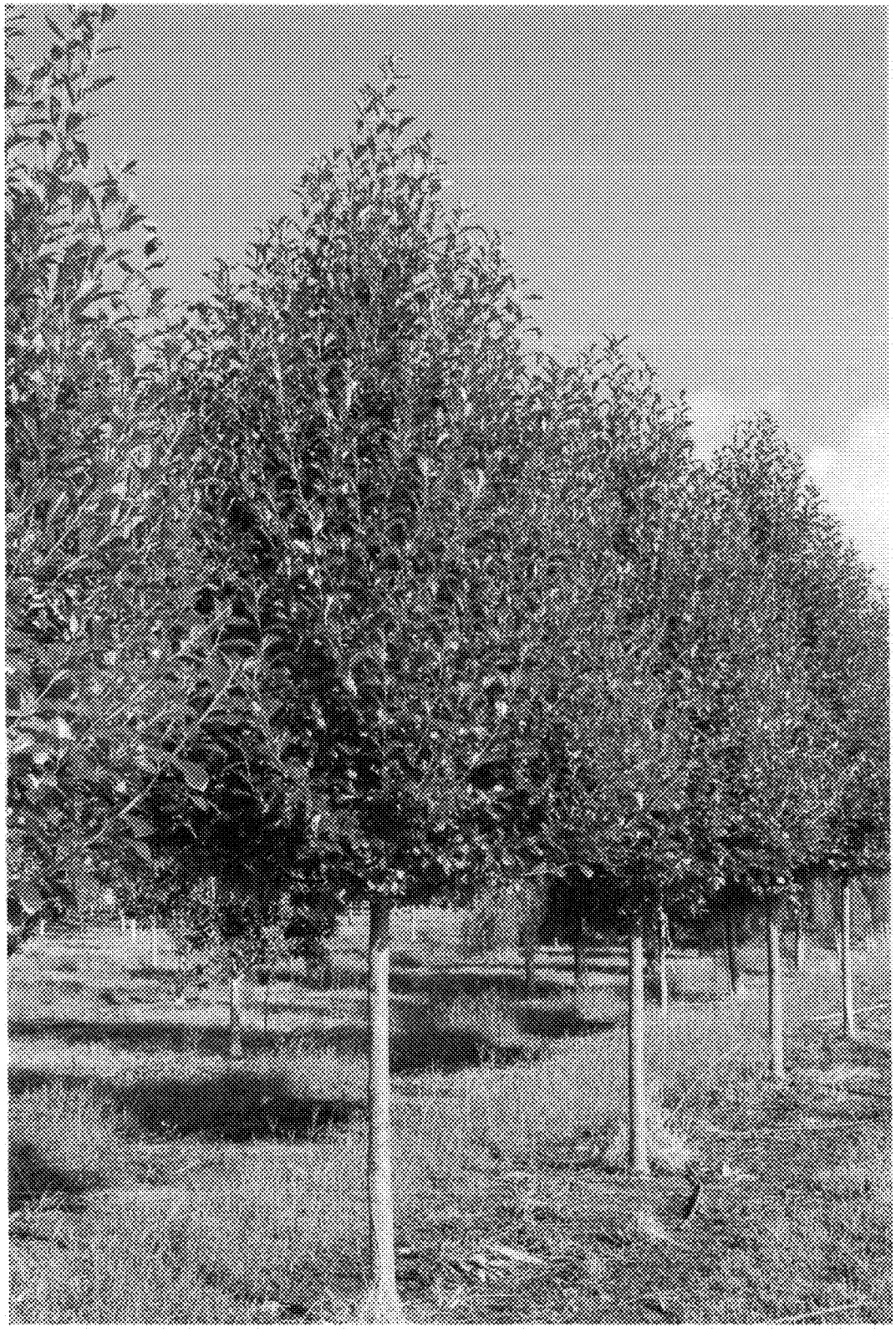

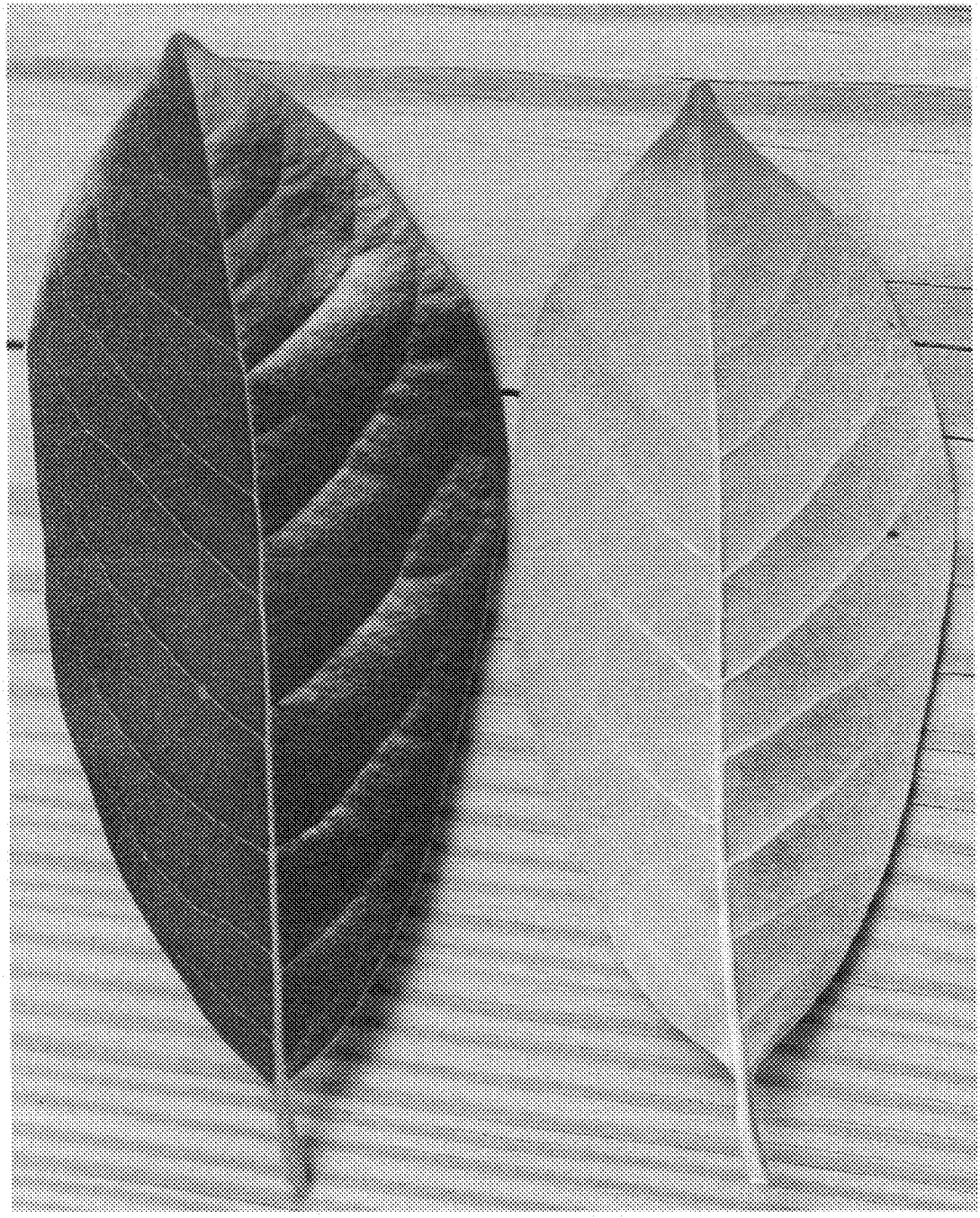

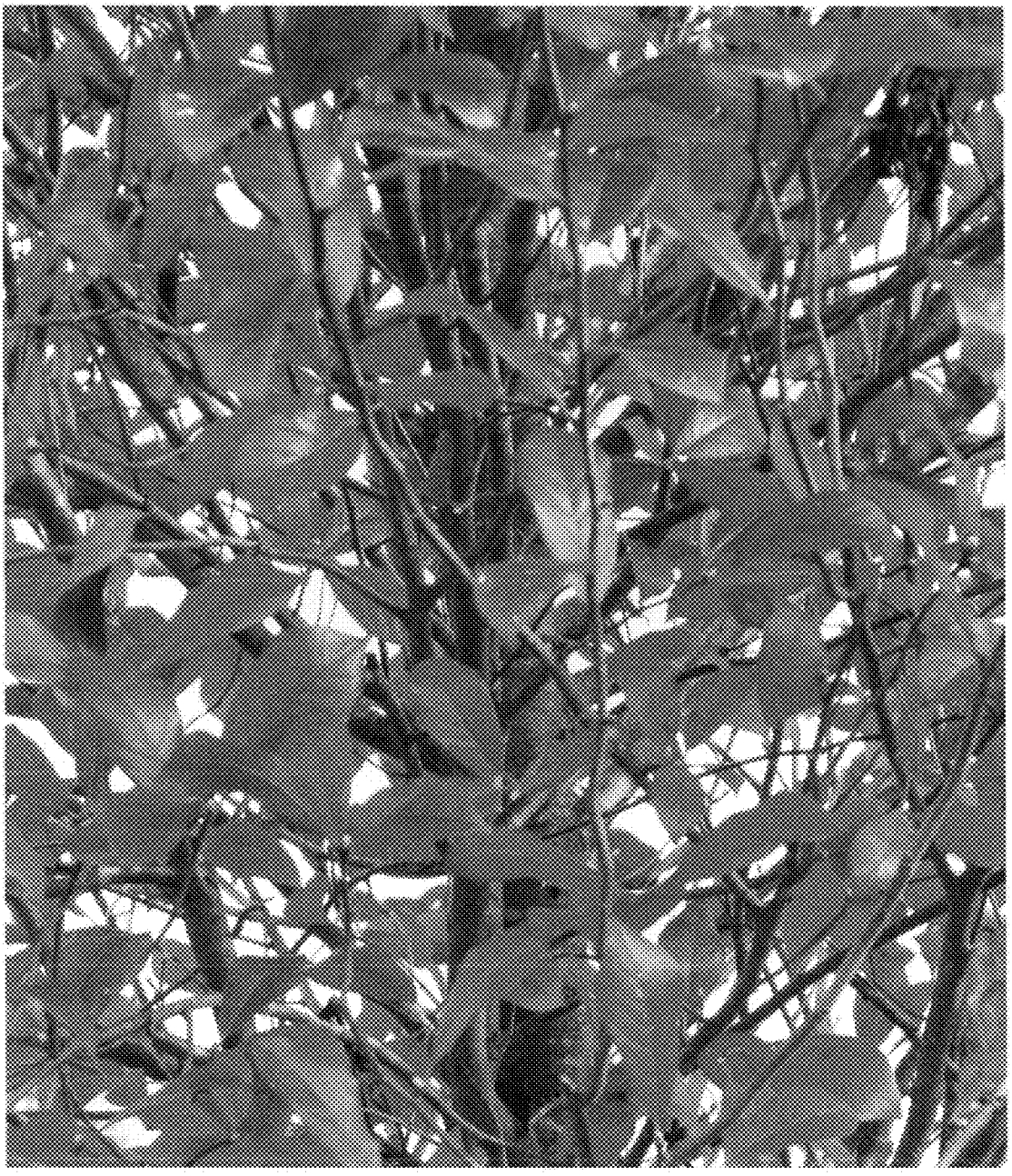

* * * * *